(12) United States Patent
Bravo et al.

(10) Patent No.: US 9,241,981 B2
(45) Date of Patent: Jan. 26, 2016

(54) USE OF A FOOD ADDITIVE BASED ON AT LEAST ONE PHYTONUTRIENT FOR STIMULATING VACCINE IMMUNITY AGAINST APICOMPLEXA IN ANIMALS

(75) Inventors: David Bravo, Yverdon-les-Bains (CH); Hyun Lillehoj, Maryland, MD (US)

(73) Assignees: PANCOSMA S.A., Le Grand Saconnex (CH); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 0 days.

(21) Appl. No.: 13/981,672

(22) PCT Filed: Jan. 31, 2012

(86) PCT No.: PCT/IB2012/000143
§ 371 (c)(1),
(2), (4) Date: Feb. 3, 2014

(87) PCT Pub. No.: WO2012/104705
PCT Pub. Date: Aug. 9, 2012

(65) Prior Publication Data
US 2014/0178437 A1    Jun. 26, 2014

Related U.S. Application Data

(60) Provisional application No. 61/438,485, filed on Feb. 1, 2011.

(51) Int. Cl.
| | | |
|---|---|---|
| *A23K 1/16* | (2006.01) | |
| *A61K 39/002* | (2006.01) | |
| *A23K 1/14* | (2006.01) | |
| *A23K 1/18* | (2006.01) | |

(52) U.S. Cl.
CPC .............. *A61K 39/002* (2013.01); *A23K 1/14* (2013.01); *A23K 1/1612* (2013.01); *A23K 1/1646* (2013.01); *A23K 1/1826* (2013.01)

(58) Field of Classification Search
None
See application file for complete search history.

(56) References Cited

U.S. PATENT DOCUMENTS

| | | | |
|---|---|---|---|
| 6,106,838 A | 8/2000 | Nitsas | |
| 6,322,825 B1 | 11/2001 | Ninkov | |
| 6,767,546 B1 * | 7/2004 | Allen et al. | ............... 424/271.1 |

FOREIGN PATENT DOCUMENTS

| | | |
|---|---|---|
| WO | 97/01348 A1 | 1/1997 |
| WO | 2008/155536 A1 | 12/2008 |

OTHER PUBLICATIONS

Lee et al. (Vet. Parasitol., 181-97-105, 2011).*
Lee et al. (Vaccine, 28:6498-6504, available online Jul. 15, 2010).*
Khalafalla, Reda E., et al., "Effects of curcumin(diferuloylmethane) on Eimeria tenella sporozoites in vitro", Parasitology Research, Oct. 13, 2010, vol. 108, No. 4, pp. 879-886.
Lee, Sung Hyen, et al., "Effect of Dietary Curcuma, Capsicum, and Lentinus, on Enhancing Local Immunity against Eimeria acervulina Infection", The Journal of Poultry Science, Jan. 1, 2010, vol. 47, No. 1, pp. 89-95.
International Search Report dated Jul. 4, 2012, issued in corresponding application No. PCT/IB2012/000143.

* cited by examiner

*Primary Examiner* — Brian J Gangle
(74) *Attorney, Agent, or Firm* — Westerman, Hattori, Daniels & Adrian, LLP

(57) ABSTRACT

The invention relates to the use of a food additive comprising at least one phytonutrient in order to stimulate vaccine immunity against *apicomplexa* in non-human monogastric animals, such as poultry or pigs, or in ruminants, such as a cattle, sheep or goats.

20 Claims, 4 Drawing Sheets

USE OF A FOOD ADDITIVE BASED ON AT LEAST ONE PHYTONUTRIENT FOR STIMULATING VACCINE IMMUNITY AGAINST APICOMPLEXA IN ANIMALS

STATEMENT REGARDING FEDERALLY SPONSORED RESEARCH OR DEVELOPMENT

This invention was made with Government support under Agreement No. 58-1265-8-103F awarded by the U.S. Department of Agriculture, Animal and Natural Resources Institute. The Government has certain rights in the invention.

The invention relates to the use of a feed additive comprising at least one phytonutrient, for stimulating vaccine immunity against *apicomplexa* in a monogastric animal, such as poultry or pigs, or in a ruminant, such as cattle, sheep or goats.

BACKGROUND OF THE INVENTION

*Apicomplexa* or sporozoa are single-cell organisms which are parasites of vertebrates or of invertebrates. These parasites can cause various pathological conditions.

For example, coccidiosis, which is an intestinal disease caused by several distinct species of the *Eimeria* protozoan, is a parasitic infection which is economically significant for the poultry industry throughout the world.

They are generally treated with drugs which are antibiotics of the sulfamide category. However, the use of this chemoprophylaxis is not without drawbacks, owing in particular to the emergence of drug-resistant *Eimeria* strains and to the complicated interaction between coccidiosis parasites and clostridial infections. Furthermore, the regulations regarding drugs are ever increasing in animal production.

Because of the complexity of the host's immunity and of the lifecycle of the parasites, it proves to be particularly difficult to develop new strategies for intervention or new vaccines against *apicomplexa*.

There is at the time no totally effective vaccine against these infections. The current tendency is therefore to use vaccines based on live parasites to control coccidiosis. At least ten vaccines of this type are commercially available worldwide. All these vaccines have recourse to infected live oocysts in order to produce a real infection which is intended to trigger a natural immunization that protects poultry.

This vaccination technique has the major drawback that live oocysts can be produced only by chickens, which requires a lot of work and involves numerous manipulations.

An alternative to vaccines of this type consists in using recombinant-protein vaccines against coccidiosis, said recombinant protein being for instance profilin which is an immunogenic protein of *Eimeria*. Recombinant vaccinations using profilin by subcutaneous immunization in young chickens or by immunization of embryos have induced a certain protection against avian coccidiosis. However, protein vaccines have a limited immunogenicity and their efficacy as a vaccine for reducing production losses due to coccidiosis is lower than that of the conventional coccidiostats and than the live oocyst-based vaccine. In any event, in order to improve the efficacy of the vaccines, various strategies have been examined, including adjuvants and cytokines.

Recent scientific publications show the direct effects of phytonutrients derived from plants on the genes involved in innate host immunity in poultry. However, numerous phytonutrients exist naturally and, for those which have been studied, they can have completely different properties from one another. For example, among the phytonutrients used in the present invention, the following are found:

- carvacrol is one of the most common components of essential oils, it has a wide antimicrobial activity, and it has been approved as a safe feed additive in the United States of America and in Europe;
- cinnamaldehyde has shown antifungal, antipyretic, antioxidant, antimicrobial and larvicidal activity, in addition to modulating T cell differentiation;
- pepper (*Capsicum* spp) reduces intestinal pro-inflammatory cytokine levels, it increases weight gain and reduces parasitic fertility in poultry infected with *E. acervulina*;
- plants of the *Curcuma* genus, including *C. longa*, exhibit antioxidant and anti-inflammatory properties, and chicken macrophages treated with *curcuma* extracts have shown increased levels of mRNA encoding IL-6 and IFN-$\gamma$.

One of the new drug-free approaches which has not been tested up until now is the combined strategy of using a vaccine with a nutrition-mediated dietary immunomodulation, in particular mediated by phytonutrients as nutritional supplements.

SUMMARIZING DESCRIPTION OF THE INVENTION

The main objective of the invention is to combat the *apicomplexa* present in the body of animals, such as poultry or ruminants, for instance cattle or goats.

The inventors have discovered, surprisingly, that it is possible to combat *apicomplexa* more successfully by stimulating the immunity induced in the host after vaccination against the infectious agent through the use of feed additives.

Furthermore, these feed additives have the advantage of being known phytonutrients which are generally easy to find commercially, such as those belonging to the terpenoid class.

Furthermore, the stimulation obtained was found not to be toxic.

The use of these nutritional supplements was found to be particularly effective since it provides synergistic effects stimulating vaccination-induced immunity.

In particular, two mixtures consisting of carvacrol/cinnamaldehyde/*capsicum* (VAC), and of *circuma/capsicum* (MC) have been successfully tested and have made it possible to show that the animals treated by supplementation with these phytonutrients, in the case in point poultry infected with coccidiosis, have in particular a much reinforced immunity, greater weight gains and much reduced excreted oocyst levels compared with the untreated animals.

Moreover, these phytonutrients have not shown any toxicity, nor any adverse effects, as is often the case with the conventional antiparasitics of drug origin.

Other features and advantages of the invention will now be described in detail in the description which follows and which is given with reference to the appended figures, the legends of which are as follows:

FIG. 1 presents the effects of the phytonutrient feed supplements VAC and MC on body weight (FIG. 1A) and oocyst excretion (FIG. 1B) in farmed chickens after infection with *E. tenella*. The columns which do not have the same letters in common are significantly different (P<0.05) according to Duncan's test.

FIG. 4 presents the effects of the phytonutrient feed supplements VAC and MC on the levels of intestinal cytokines produced. For this, the mRNA level is quantified for each of the following cytokines: IFN-γ in FIG. 4A, IL-6 in FIG. 4B, IL-17F in FIG. 4C, and TNFSF15 in FIG. 4D, and these levels are normalized relative to the level of mRNA encoding GAPDH In FIGS. 2, 3 and 4, each column represents the mean±standard deviation with 4 replications per treatment (N=4 chickens/group). The columns which do not have the same letters in common are significantly different (P<0.05) according to Duncan's test.

DETAILED DESCRIPTION OF THE INVENTION

The present invention relates to a feed additive for stimulating vaccine immunity in non-human animals infected with an *Apicomplexa sporozoan*, comprising at least one phytonutrient.

The expression "stimulating vaccine immunity" means that the animals are vaccinated against the infectious agent as prevention against the disease linked to an apicomplex pathogen.

The term "phytonutrient" is intended to mean any plant-derived bioactive compound which has positive effects on animal health.

Among the phytonutrients targeted by the present invention, there are in particular those of the group of plant terpenoids, some of which are known and used because of their aromatic qualities (such as essential oils), but also for their various antiseptic, antioxidant, antifungal, antimicrobial and/or larvicidal properties.

The inventors have shown, with their studies carried out on several of them, that they can surprisingly amplify immune protection against infectious agents when they are used together with vaccine immunization.

According to one preferred embodiment of the invention, the supplementation is carried out by adding at least one phytonutrient chosen from carvacrol, cinnamaldehyde, *capsicum* and curcumin. These phytonutrients can be used alone or in combination.

As preferred phytonutrients according to the invention, mention may in particular be made of the carvacrol/cinnamaldehyde combination, and also the *curcuma/capsicum* combination.

As *capsicum*, use is generally made of pepper (*Capsicum annum* or *Capsicum frutescens*), normally in oleoresin form.

The inventors of the present invention have shown, during in vivo tests, their synergistic effects via stimulation of the protective immunity after vaccination against the infectious agent, surprisingly given their completely different properties previously acknowledged (mentioned in the "background of the invention" section). This resulted, in the hosts having received the supplementation compared with those which have not received it, in, in particular, a much greater weight gain, a reduction in excreted oocysts, an increase in antibody response and significantly reduced levels of several pro-inflammatory cytokines, which had not been shown in the prior art, nor even suggested.

The invention also relates to a feed for non-human animals which is intended for preventing infectious diseases linked to the *Apicomplexa sporozoan*, comprising, in addition to a preferably balanced feed intake, a supplementation in at least one phytonutrient.

A balanced feed intake consists in providing all the nutrients that poultry (chicks, young and adults) need during their growth and cramming, in terms of proteins, carbohydrates and lipids, but also vitamins and minerals. Generally, it consists of cereal flour, oil-producing plant meal and protein-producing plant meal, to which supplements such as vitamins and trace elements can be added.

Advantageously, the supplementation of the feed intake is carried out with at least one phytonutrient chosen from carvacrol, cinnamaldehyde, *capsicum* and curcumin, used alone or in combination.

Even more advantageously, it is carried out with the carvacrol/cinnamaldehyde/*capsicum* combination or with the *curcuma/capsicum* combination.

In the context of the invention, the phytonutrients will be used according to a total phytonutrient(s) concentration of between 1 and 50 mg per kilogram of feed intake or between 0.5 and 20 mg per liter of drinking water.

According to the invention, the supplementation can be carried out in solid form, i.e. by addition to the feed intake, or else in liquid form by addition to the drinking water. Advantageously, the supplemented feed for non-human animals of the invention is in the form of powder, of granules or of tablets.

It is preferentially intended for poultry.

The vaccination is carried out as early as possible, preferably as soon as the animals are 1 day old.

The immunization of the hosts, in particular the poultry, is carried out by vaccination. The vaccine which is combined with the phytonutrient supplementation can be derived from recombinant protein. By way of example, the recombinant protein vaccine originates from profilin, which is an immunogenic protein of *Eimeria* and which has previously been shown to induce significant protection against avian coccidiosis and to reduce fertility of the parasite.

The type of vaccine used in the examples served as a model. However, at the current time, it is not the main vaccine type available. The vaccines predominantly used are derived from attenuated oocysts.

Other types of vaccines are also possible according to the invention. Conclusive tests have been carried out with a combination of "live attenuated vaccine" and phytonutrients.

The host vaccination can be carried out by various routes of inoculation (subcutaneous, systemic, etc.), but the oral route is quite obviously the one which is preferred since not only does it make it possible to obtain good results in terms of immunogenicity, but it is also practical; all that is required is to simply add the vaccine solution to the drinking water, as is commonly the case on farms.

The vaccines can also be in the form of a gel which is sprayed directly onto the animals, for example the chicks, which ingest it by contact.

The feed additive or nutritional supplement of the present invention and also the feed or the drinking water containing it are suitable for preventing, in non-human animals, infectious diseases linked to sporozoa belonging to the *Apicomplexa* genus, among which in particular are the agents for coccidiosis (*coccidia*); for toxoplasmosis (*toxoplasma*); cryptosporidiosis (*cryptosporidia*); malaria (*plasmodium*); neosporosis (*Neospora*).

The invention applies quite particularly to combating coccidiosis, which can be caused by various species of *Eimeria*, including those which affect chickens/laying hens (*E. tenella, E. acervulina, E. brunette, E. maxima, E. mitis, E. necatrix, E. praecox*); those which affect turkeys (*E. meleagrimitis, E. adenoeides, E. dispersa, E. gallopavonis*); those which affect geese (*E. truncata, E. anseris*); those which affect ducks (*E. tyzzeria perniciosa, E. mulardi*); those which affect guinea-poultry (*E. Numidia, E. grenieri*); or that which affects pigeons (*E. labbeana*).

The invention applies to non-human animals to which these apicomplex-linked diseases relate and for which vaccine immunization against these infectious agents exists.

These animals may be monogastric, such as poultry, pigs or rabbits, or be ruminants, such as cattle, sheep or goats.

It applies in particular to poultry.

Among the poultry, mention may preferably be made of chickens/laying hens, but also turkeys, geese, ducks, guinea-poultry, quail, pheasants and pigeons. These are farm animals intended for human food which can be kept in cages arranged in batteries on the ground, or in henhouses, or which live in the open or are free range. The important thing is to be able to provide them daily with feed supplemented with phytonutrients; these animals having received an immune vaccination against the sporozoa mentioned above.

EXAMPLES

A comparison was made between two different mixtures of phytonutrients originating from plants as feed additives in order to stimulate a host vaccine response during a recombinant antigen vaccination: VAC is composed of 5 mg of carvacrol, 3 mg of cinnamaldehyde and 2 mg of *capsicum* oleoresin per kg of feed intake, while MC is composed of 4 mg of *curcuma* oleoresin and 4 mg of *capsicum* oleoresin per kg of feed intake.

The synergistic effect of the feed supplementation with VAC and with MC on the immunization with profilin against avian coccidiosis was evaluated by examining the body weight, fecal oocysts excretion, splenocyte subpopulations and cytokine levels.

The abbreviations used in the text are the following:

EO=phytonutrients;

CON=control animals, i.e. animals not infected, not vaccinated, not fed with plant extracts;

CON infected with *Eimeria tenella*=animals not having had a vaccination, not fed with phytonutrients, but infected with *Eimeria tenella*;

CON-V infected with *Eimeria tenella*=animals having had a vaccination, not fed with phytonutrients, but infected with *Eimeria tenella*;

CON-VAC-V infected with *Eimeria tenella*=animals having had a vaccination, fed with carvacrol, cinnamaldehyde and *capsicum* oleoresin, and infected with *Eimeria tenella*;

CON-MC-V infected with *Eimeria tenella*=animals having had a vaccination, fed with *curcuma* and *capsicum* oleoresins and infected with *Eimeria tenella*.

Animal Experiments and Feed Intakes

All the experiments were approved by the USDA's Agriculture Research Service Institutional Animal Care and Use Committee (ARS IACUC). Young day-old chickens (Ross/Ross, Longenecker's hatchery, Elizabethtown, Pa.) were placed in Petersime incubators and randomly divided up into 4 groups (12 chickens/group). They had free access to a standard feed intake (CON and CON-V) or to standard feed intakes supplemented with VAC or MC for 27 days after hatching.

The chickens were kept in a heat-controlled environment (29° C.). All the feed intakes contained 24.2% of raw protein, 54.0% of carbohydrates, 15% of a mixture of vitamins and minerals, 4.7% of fats and 2.4% of fibers (USDA/FeedMill, Beltsville, Md.).

The chickens of the vaccinated groups were immunized with profilin (CON-V, VAC-C, MC-V) at 7 days old, and the animals were infected with coccidiae at 17 days old by oral inoculation of $2.0 \times 10^4$ sporulated *Eimeria tenella* oocysts as previously described in the literature. The chickens were previously raised in *Eimeria*-free facilities for 2 weeks, and then transferred into cages (2 chickens/cage) and kept until the end of the experimental period in premises separate from those in which they had been infected.

Statistical Analyses

The statistical analyses were carried out using the SPSS® software (SPSS 15.0 for Windows®, Chicago, Ill.) and all the data were expressed as means±mean standard deviation. The comparisons of the mean values were carried out by one-way analysis of variance, followed by Duncan's multiple range significance test, and the differences were considered to be statistically significant at $P<0.05$.

Example 1

Effect of VAC and MC Supplementation on Body Weight

Method

Body weight was measured on day 0 and 9 post-infection (DPI). In order to assay the excreted fecal oocysts, the chickens were placed in special cages for collecting oocysts (2 chickens/cage, 12 chickens/group) and fecal samples were collected from day 5 to day 9 post-infection.

Results

Figure 1A:
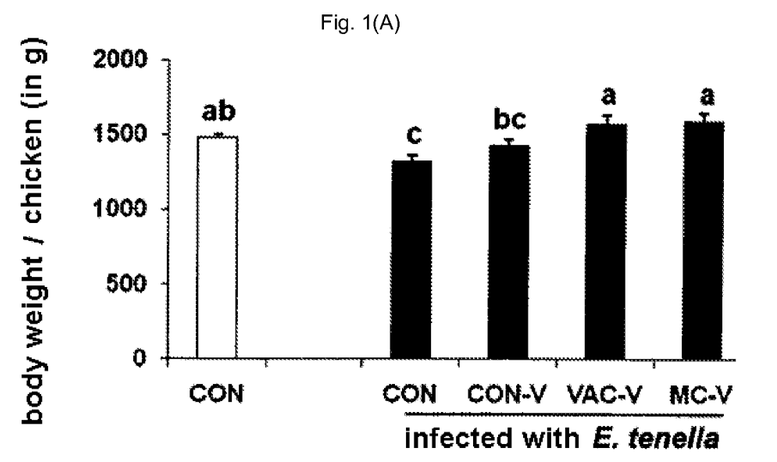

The feeding of the farmed chickens with an intake supplemented with VAC and with MC exhibited no toxic effect in the host according to the body weight modifications and other physical characteristics at the doses used during this trial. During the first 17 days after hatching, the chickens which had received the supplemented intakes did not show any change in the level of their body weight, compared with those which had received the standard intake alone. After infection with *E. tenella* (day 10 post-infection), however, the chickens immunized with the vaccine against profilin (CON-V, VAC-V, MC-V) exhibited body weights which were 8 to 21% higher compared with the infected controls which had received the unsupplemented intake (CON, FIG. 1A). In comparison with the CON group, a significant difference was observed only in the VAC-V and MC-V groups vaccinated with profilin and supplemented with phytonutrients, which showed body weights which were, respectively, 20% and 21% higher. These results clearly demonstrate the synergistic effects of the nutritional supplementation with phytonutrients on the vaccination with profilin against avian coccidiosis in young farmed chickens.

Example 2

Effect of VAC and MC Supplementation on Fecal Oocyst Excretion

Methods

The numbers of oocysts were determined as previously described in the literature using a MacMaster cell and according to the following formula: total oocysts/chicken=[number of oocysts×dilution factor×(volume of the fecal sample/volume of the counting cell)]/2.

Results

Figure 1B:
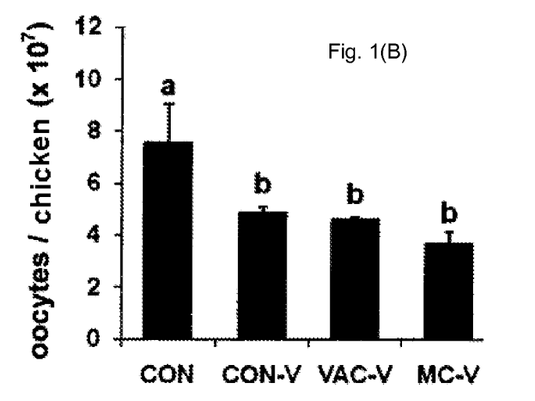

As can be seen in FIG. 1B, the fecal oocyst excretion was significantly reduced by 31 to 51% in the groups immunized against profilin and supplemented with phytonutrients. The total excreted oocysts were $4.9 \times 10^7$, $4.6 \times 10^7$ and $3.7 \times 10^7$/chicken, respectively in the CON-V, VAC-V and MC-V groups compared with the CON standard intake group which produced $9.5 \times 10^7$ oocysts/chicken. No oocyst was detected in the noninfected control chickens. These results showed that the supplementation of phytonutrients in young chickens stimulates the host's protective vaccine immune response against Eimeria tenella.

Example 3

Effect of the VAC and MC Supplementation on the Antibody Responses to Profilin Methods Blood samples (4 chickens/group) were collected by cardiac puncture immediately after euthanasia on day 10 postinfection, and the sera were obtained by centrifugation and were analyzed by ELISA in order to measure the specific antibody responses to profilin as previously described in the literature. Succinctly, 96-well microtitration plates were coated overnight with 1.0 µg/well of a purified recombinant profilin. The plates were rinsed with phosphate buffered saline containing 0.05% of TWEEN® surfactant (PBS-T) and blocked with PBS containing 1% of BSA. The diluted sera (1:50) were added (100 µl/well), incubated with shaking for 2 hours at ambient temperature and rinsed with PBS-T. The bound antibodies were detected using peroxidase-conjugated rabbit anti-chicken IgGs and the 3,3',5,5'-tetramethylbenzidine substrate (Sigma®, St Louis, Mo.). The optical density (OD) was measured at 450 nm (OD 450) using an automated microplate reader (Bio-Rad®, Richmond, Calif.). All the samples were analyzed in quadruplicate.

Results

Figure 2:
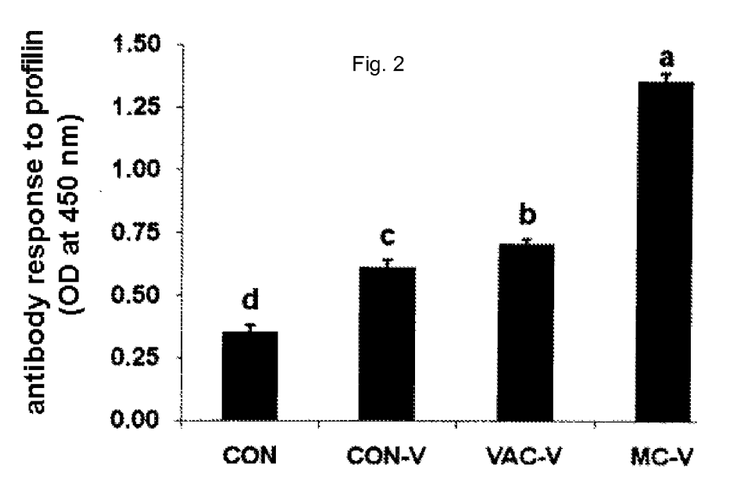
FIG. 2 presents the effects of the phytonutrient feed supplements VAC and MC on the serum antibody responses to profilin in farmed chickens infected with *E. tenella;*

On day 10 post-infection, the serum antibody titers increased in the groups vaccinated with profilin (from 0.61±0.03 to 1.36±0.04) compared with the nonvaccinated CON group (0.35±0.03), and a significant difference compared with CON-V was found in the VAC-V and MC-V groups, which exhibited an OD respectively of 0.71±0.02 and 1.36±0.04 after vaccination with the vaccine against profilin (FIG. 2). The MC-V group exhibited the highest value.

Example 4

Effect of the VAC and MC Supplementation on Splenic Lymphocyte Proliferation Methods On day 10 post-infection, the chickens (4 chickens/group) were euthanized by cervical dislocation, and the spleens were removed and placed in Petri dishes with 10 ml of Hank's balanced salt solution supplemented with 100 U/ml of penicillin and 100 µg/ml of spectromycin (Sigma®, St Louis, Mo.). The cell suspensions were prepared by careful rinsing on a cell screen and the lymphocytes were purified by density gradient centrifugation on HISTOPAQUE®-1077 medium (Sigma®). The number of cells was adjusted to a concentration of $5.0 \times 10^6$ cells/ml; said cells were placed in RPMI medium containing 10% of fetal bovine serum, 100 U/ml of penicillin and 100 µg/ml of streptomycin and incubated in 20 µg/ml of profilin in 96-well plates in a humidified incubator (Forma, Marietta, Ohio) at 41° C. and 5% $CO_2$ for 24 hours. The cell proliferation was measured using the WST-8® cell counting kit (Dojindo Molecular Technologies, Gaithersburg, Md.) at 450 nm using a microplate spectrophotometer (BioRad®, Hercules, Calif.) as described previously in the literature. The lymphocyte proliferation was expressed as stimulation index, which is the ratio of the mean OD value of the group stimulated with profilin divided by the mean OD value of the group stimulated only with the medium CON.

Results

Figure 3:
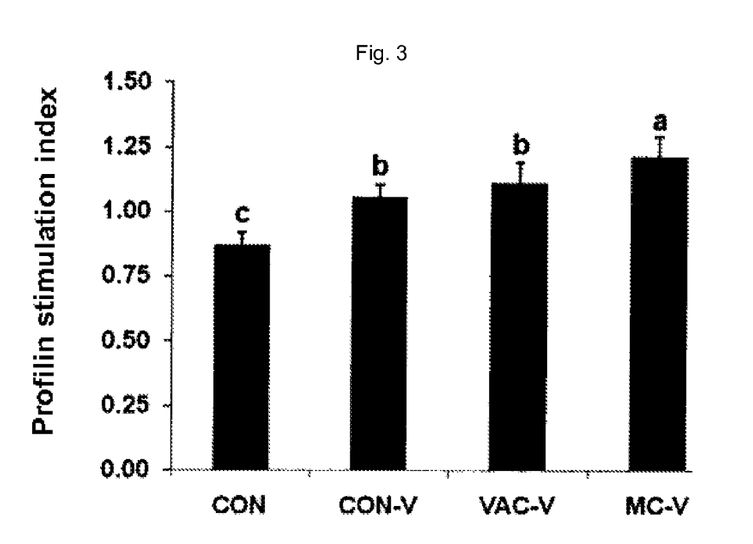
FIG. 3 presents the effects of the phytonutrient feed supplements VAC and MC on splenic-lymphocyte proliferation in farmed chickens infected with *E. tenella;*
Figure 4A:
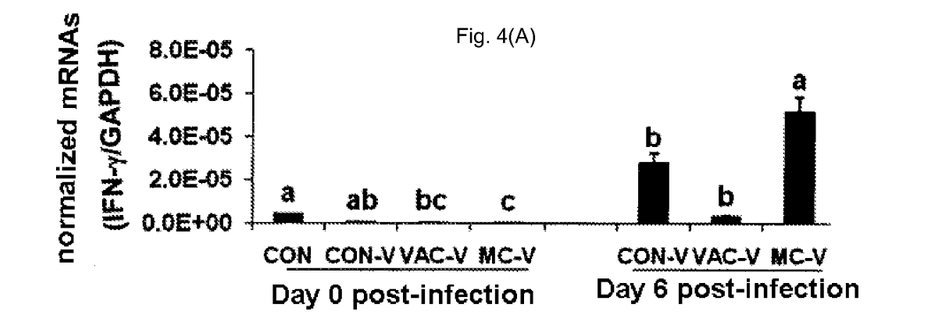
Figure 4B:
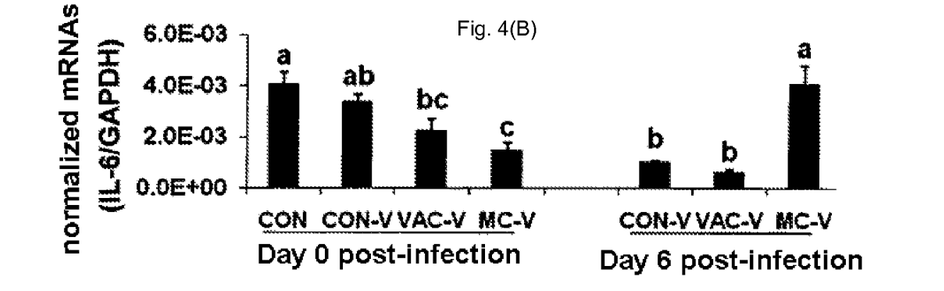
Figure 4C:
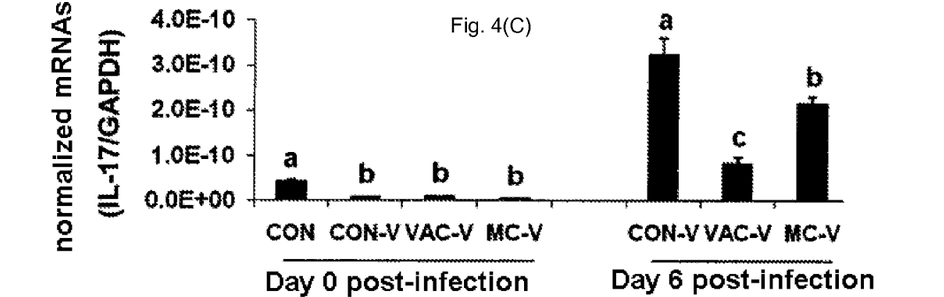
Figure 4D:
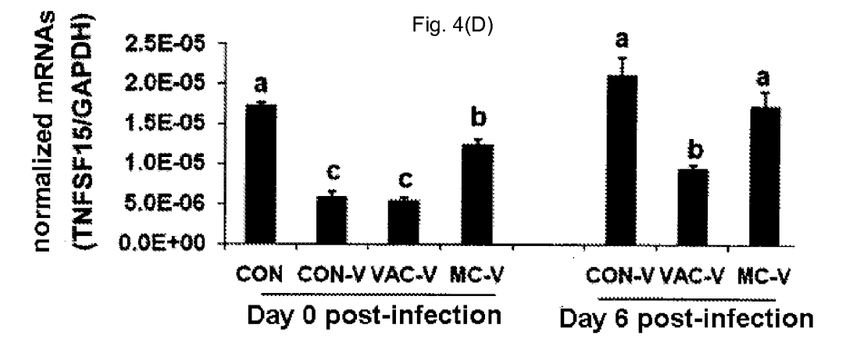

The lymphocyte proliferative response of the splenocytes, caused by the antigen, as expressed by the stimulation index, was increased in the groups vaccinated with profilin (from 1.05±0.05 to 1.21±0.11) compared with the nonimmunized CON group (0.87±0.01) on day 10 post-infection (FIG. 3). The MC-V group exhibited the highest value.

Example 5

Effect of the VAC and MC Supplementation on Cytokine Production

Methods

Cecal tonsils were obtained from noninfected and infected chickens which were fed with control (CON-V) and phytonutrient-supplemented (VAC and MC-V) feed intakes, on day 0 and day 6 post-infection (4 chickens/group), and the expression of their genes encoding cytokines was determined using RTQ-PCR as previously described in the literature. Intestines were removed, cut lengthwise, and washed three times with ice-cold Hank's balanced salt solution (HBSS) containing 100 U/ml of penicillin and 100 µg/ml of streptomycin. The mucosal layer was removed by meticulous scraping using a surgical scalpel and the tissue was washed with HBSS. The total RNA was extracted from the mucosal layer using TRIZOL® reagent (Invitrogen®, Carlsbad, Calif.). Five micrograms of total RNA were treated with 1.0 U of DNAse I and 1.0 µl of 10× reaction buffer (Sigma®) and incubated for 15 minutes at ambient temperature. After incubation, 1.0 µg of stop solution was added in order to inactivate the DNAse I, and the mixture was heated at 70° C. for 10 minutes. The RNA was subjected to reverse transcription using the STRATASCRIPT® $1^{st}$ strand synthesis system (Stratagene®, La Jolla, Calif.) according to the maker's recommendations. The RT-PCR oligonucleotide primers for the chicken cytokines and the GAPDH internal control are indicated in the table hereinafter.

| RNA target | Primer sequences | PCR product size (in bp) | Accession No. |
|---|---|---|---|
| GAPDH | F: 5'-GGTGGTGCTAAGCGTGTTAT-3' (SEQ ID NO: 1)<br>R: 5'-ACCTCTGTCATCTCTCCACA-3' (SEQ ID NO: 2) | 264 | K01458 |
| IFN-γ | F: 5'-AGCTGACGGTGGACCTATTATT-3' (SEQ ID NO: 3)<br>R: 5'-GGCTTTGCGCTGGATTC-3' (SEQ ID NO: 4) | 259 | Y07922 |

-continued

| RNA target | Primer sequences | PCR product size (in bp) | Accession No. |
|---|---|---|---|
| IL-6 | F: 5'-CAAGGTGACGGAGGAGGAC-3' (SEQ ID NO: 5)<br>R: 5'-TGGCGAGGAGGGATTTCT-3' (SEQ ID NO: 6) | 254 | AJ309540 |
| IL-17F | F: 5'-CTCCGATCCCTTATTCTCCTC-3' (SEQ ID NO: 7)<br>R: 5'-AAGCGGTTGTGGTCCTCAT-3' (SEQ ID NO: 8) | 292 | AJ493595 |
| TNFSF15 | F: 5'-CCTGAGTATTCCAGCAACGCA-3' (SEQ ID NO: 9)<br>R: 5'-ATCCACCAGCTTGATGTCACTACC-3' (SEQ ID NO: 10) | 292 | NM010245578 |

The amplification and the detection were carried out using equivalent amounts of total RNA by virtue of the MX3000P® PCR system and the Brilliant SYBR® Green dye qPCR mixture (Stratagene®). The standard curves were generated using log 10-diluted standard RNA. The individual transcript levels were then normalized with respect to those of GAPDH and analyzed using the Q-GENE® program. Each analysis was carried out in triplicate. In order to normalize the individual replicas, the cycle threshold (Ct) values on the logarithmic scale were converted into linear units of normalized expression prior to the calculation means and to the SEM (standard error of the mean) for the individual targets and references, followed by determination of the mean normalized expression (MNE) using the Q-GENE® program as described in the prior art.

Results

FIG. 4 demonstrates the effect of the supplementation of the feed intake with VAC and with MC on the production of cecal cytokines after immunization with the profilin vaccine. The profilin-vaccinated groups having received feed with VAC and MC showed, on the whole, a reduction in IFN-γ, IL-6, IL-17F and TNFSF15 pro-inflammatory cytokines in the ceca compared with the nonvaccinated CON group (P<0.05). The levels of cecal IFN-γ, IL-17F and TNFSF15 cytokines increased after oral challenge infection with *E. tenella* compared with their values before infection. It is interesting to note that the IFN-γ and IL-6 levels in the profilin-vaccinated group fed with the MC-supplemented feed increased significantly compared with the CON-V group on day 6 post-infection. The level of intestinal IL-17F decreased significantly in the VAC-V and MC-V groups, whereas the level of TNFSF15 decreased significantly in the VAC-V group compared with the CON-V group.

These results showed that the mixtures of VAC and MC phytonutrients operate synergistically with the profilin vaccine so as to have a significant impact on the levels of local cytokines produced.

Example 6

Effect of the Supplementation with VAC and MC on Proliferal Blood Lymphocyte Subpopulations Methods On day 10 post-infection, the chickens were killed by cervical dislocation and bled by cardiac puncture using a heparinized syringe. The suspensions of individual peripheral blood lymphocyte (PBL) cells were prepared as described previously in the literature, placed in suspension in HBSS without phenol red, supplemented with 3% of HYCLONE® fetal bovine serum (Thermo Scientific, Logan, Utah) and 0.01% of sodium azide (FCA buffer), and their number was adjusted to a concentration of $1 \times 10^7$/ml in FCA buffer. The cells were incubated for 30 minutes in ice with mouse monoclonal antibodies (mAbs) specific for chicken major histocompatibility complex (MHC) class II, for CD4, or CD8, for K1, for T cell receptor 1 (TCR1) or for T cell receptor 2 (TCR2) of chicken. As a negative control, HB2, which is an antibody specific for human T cells (American Type Culture Collection, ARS-USDA) was included and an antibody against C6B12, which is a chicken MHC class 1 antigen, was used as a positive control. After incubation, the cells were rinsed three times with FCA buffer and incubated with 100 µl of goat anti-mouse IgG secondary antibody labeled with fluorescein isothiocyanates (Sigma®), for 45 minutes on ice. The cells were rinsed three times with FCA buffer and the fluorescence was then analyzed on $1 \times 10^4$ viable cells using a FACSCALIBUR® analyzer (BD Science, Boston).

Results

The percentages of the peripheral blood lymphocyte subpopulations in the farmed chickens are given in the table hereinafter.

| Monoclonal antibody (mAb) | CON-V group | CON-VAC-V group | CON-MC-V group |
|---|---|---|---|
| MHC2 | 21.3 ± 1.8b | 18.6 ± 1.1b | 54.7 ± 4.1a |
| CD4 | 17.3 ± 1.6b | 16.2 ± 1.1b | 32.8 ± 1.8a |
| CD8 | 23.3 ± 1.8b | 23.3 ± 1.9b | 44.2 ± 3.5a |
| HUM | 2.1 ± 0.1b | 3.9 ± 0.2a | 1.8 ± 0.1b |
| TCR1 | 3.6 ± 0.3b | 2.8 ± 0.1b | 9.0 ± 0.6a |
| TCR2 | 9.1 ± 0.5b | 13.4 ± 0.8b | 30.0 ± 1.6a |

In the profilin-vaccinated group having received the MC-supplemented feed intake, the percentages of T lymphocytes expressing MHC class II, CD4, CD8, TCR1 and TCR2 were significantly increased compared with those of the CON-V and CON-VAC-V groups on day 10 post-infection; most of the values being double those of the CON-V and CON-MC-V groups.

In contrast, the percentage of cells expressing a macrophage marker K1de was significantly increased in the CON-VAC-V group compared with that of the CON-V and CON-VAC-V groups on day 10 post-infection.

The invention claimed is:

1. A method of stimulating vaccine immunity against *apicomplexa* comprising administering a feed additive comprising at least one phytonutrient to a non-human animal so as to stimulate vaccine immunity against *apicomplexa* in the non-human animal,
   wherein the at least one phytonutrient is chosen from the group consisting of carvacrol, cinnamaldehyde, *capsicum*, curcumin and mixtures of two or more of these compounds, and
   wherein the vaccine immunity is obtained by means of a vaccine.

2. The method as claimed in claim 1, wherein the feed additive comprises carvacrol, cinnamaldehyde and *capsicum* oleoresin.

3. The method as claimed in claim 1, wherein the feed additive comprises *curcuma* and *capsicum* oleoresin.

4. The method as claimed in claim 1, wherein the feed additive is present in a feed or in a drinking water of the animal.

5. The method as claimed in claim 1, wherein a concentration of the at least one phytonutrient is between 1 and 50 mg per kilogram of feed intake or between 0.5 and 20 mg per liter of drinking water.

6. The method as claimed in claim 1, wherein the feed additive is in the form of powder, of granules or of tablets.

7. The method as claimed in claim 1, wherein the animal is a monogastric animal.

8. The method as claimed in claim 7, wherein the animal is a poultry.

9. The method as claimed in claim 1, wherein the animal continuously ingests the feed additive.

10. The method as claimed in claim 1, wherein the vaccine is derived from recombinant protein.

11. The method as claimed in claim 10, wherein the vaccine derived from recombinant protein is a profilin-based vaccine.

12. The method as claimed in claim 1, comprising stimulating vaccine immunity against coccidiosis caused by *apicomplexa*.

13. The method as claimed in claim 2, wherein the feed additive is present in a feed or in a drinking water of the animal.

14. The method as claimed in claim 2, wherein a concentration of the at least one phytonutrient is between 1 and 50 mg per kilogram of the feed or between 0.5 and 20 mg per liter of the drinking water.

15. The method as claimed in claim 2, wherein the feed additive is in the form of powder, of granules or of tablets.

16. The method as claimed in claim 3, wherein the feed additive is present in a feed or in a drinking water of the animal.

17. The method as claimed in claim 3, wherein a concentration of the at least one phytonutrient is between 1 and 50 mg per kilogram of the feed or between 0.5 and 20 mg per liter of the drinking water.

18. The method as claimed in claim 3, wherein the feed additive is in the form of powder, of granules or of tablets.

19. The method as claimed in claim 1, wherein the non-human animals are vaccinated when the non-human animals are 1 day old.

20. The method as claimed in claim 1, wherein the non-human animals are vaccinated when the non-human animals are 7 days old.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: gallus gallus
<220> FEATURE:
<221> NAME/KEY: primer_bind
<223> OTHER INFORMATION: Designed forward primer for GAPDH gene
<300> PUBLICATION INFORMATION:
<308> DATABASE ACCESSION NUMBER: Genbank K01458
<309> DATABASE ENTRY DATE: 1993-04-28

<400> SEQUENCE: 1
ggtggtgcta agcgtgttat                                               20

<210> SEQ ID NO 2
<211> LENGTH: 20
<212> TYPE: DNA
<213> ORGANISM: gallus gallus
<220> FEATURE:
<221> NAME/KEY: primer_bind
<223> OTHER INFORMATION: Designed reverse primer for GAPDH gene
<300> PUBLICATION INFORMATION:
<308> DATABASE ACCESSION NUMBER: Genbank K01458
<309> DATABASE ENTRY DATE: 1993-04-28

<400> SEQUENCE: 2
acctctgtca tctctccaca                                               20

<210> SEQ ID NO 3
<211> LENGTH: 22
<212> TYPE: DNA
<213> ORGANISM: gallus gallus
<220> FEATURE:
<221> NAME/KEY: primer_bind
<223> OTHER INFORMATION: Designed forward primer for IFN-? gene
<300> PUBLICATION INFORMATION:
<308> DATABASE ACCESSION NUMBER: Genbank Y07922
<309> DATABASE ENTRY DATE: 2006-11-14

<400> SEQUENCE: 3
agctgacggt ggacctatta tt                                            22

<210> SEQ ID NO 4
<211> LENGTH: 17
<212> TYPE: DNA
<213> ORGANISM: gallus gallus
<220> FEATURE:
<221> NAME/KEY: primer_bind
<223> OTHER INFORMATION: Designed reverse primer for IFN-? gene
<300> PUBLICATION INFORMATION:
<308> DATABASE ACCESSION NUMBER: Genbank Y07922
<309> DATABASE ENTRY DATE: 2006-11-14

<400> SEQUENCE: 4
ggctttgcgc tggattc                                                  17

<210> SEQ ID NO 5
<211> LENGTH: 19
<212> TYPE: DNA
<213> ORGANISM: gallus gallus
<220> FEATURE:
<221> NAME/KEY: primer_bind
<223> OTHER INFORMATION: Designed forward primer for IL-6 gene
<300> PUBLICATION INFORMATION:
<308> DATABASE ACCESSION NUMBER: Genbank AJ309540
<309> DATABASE ENTRY DATE: 2005-04-15

<400> SEQUENCE: 5

```
caaggtgacg gaggaggac                                                19
```

<210> SEQ ID NO 6
<211> LENGTH: 18
<212> TYPE: DNA
<213> ORGANISM: gallus gallus
<220> FEATURE:
<221> NAME/KEY: primer_bind
<223> OTHER INFORMATION: Designed reverse primer for IL-6 gene
<300> PUBLICATION INFORMATION:
<308> DATABASE ACCESSION NUMBER: Genbank AJ309540
<309> DATABASE ENTRY DATE: 2005-04-15

<400> SEQUENCE: 6

```
tggcgaggag ggatttct                                                 18
```

<210> SEQ ID NO 7
<211> LENGTH: 21
<212> TYPE: DNA
<213> ORGANISM: gallus gallus
<220> FEATURE:
<221> NAME/KEY: primer_bind
<223> OTHER INFORMATION: Designed forward primer for IL-17F gene
<300> PUBLICATION INFORMATION:
<308> DATABASE ACCESSION NUMBER: Genbank AJ493595
<309> DATABASE ENTRY DATE: 2005-04-15

<400> SEQUENCE: 7

```
ctccgatccc ttattctcct c                                             21
```

<210> SEQ ID NO 8
<211> LENGTH: 19
<212> TYPE: DNA
<213> ORGANISM: gallus gallus
<220> FEATURE:
<221> NAME/KEY: primer_bind
<223> OTHER INFORMATION: Designed reverse primer for IL-17F gene
<300> PUBLICATION INFORMATION:
<308> DATABASE ACCESSION NUMBER: Genbank AJ493595
<309> DATABASE ENTRY DATE: 2005-04-15

<400> SEQUENCE: 8

```
aagcggttgt ggtcctcat                                                19
```

<210> SEQ ID NO 9
<211> LENGTH: 21
<212> TYPE: DNA
<213> ORGANISM: gallus gallus
<220> FEATURE:
<221> NAME/KEY: primer_bind
<223> OTHER INFORMATION: Designed forward primer for TNFSF15 gene
<300> PUBLICATION INFORMATION:
<308> DATABASE ACCESSION NUMBER: Genbank NM010245578
<309> DATABASE ENTRY DATE: 2013-08-27

<400> SEQUENCE: 9

```
cctgagtatt ccagcaacgc a                                             21
```

<210> SEQ ID NO 10
<211> LENGTH: 24
<212> TYPE: DNA
<213> ORGANISM: gallus gallus

```
-continued

<220> FEATURE:
<221> NAME/KEY: primer_bind
<223> OTHER INFORMATION: Designed reverse primer for TNFSF15 gene
<300> PUBLICATION INFORMATION:
<308> DATABASE ACCESSION NUMBER: Genbank NM010245578
<309> DATABASE ENTRY DATE: 2013-08-27

<400> SEQUENCE: 10
atccaccagc ttgatgtcac taac                                          24
```